United States Patent [19]

Ross et al.

[11] Patent Number: 5,783,199

[45] Date of Patent: Jul. 21, 1998

[54] ANAESTHETIC MIXTURES CONTAINING ENFLURANE OR ISOFLURANE IN COMBINATION WITH SEVOFLURANE OR DESFLURANE

[75] Inventors: John Alexander Strachen Ross, Aberdeen; Michael Eric Tunstall, Newtonhill, both of Scotland

[73] Assignee: British Technology Group Ltd., London, England

[21] Appl. No.: 809,040

[22] PCT Filed: Aug. 25, 1995

[86] PCT No.: PCT/GB95/02021

§ 371 Date: Mar. 7, 1997

§ 102(e) Date: Mar. 7, 1997

[87] PCT Pub. No.: WO96/08241

PCT Pub. Date: Mar. 21, 1996

[30] Foreign Application Priority Data

Sep. 14, 1994 [GB] United Kingdom .................. 9418532

[51] Int. Cl.⁶ ........................................................ A61K 9/00
[52] U.S. Cl. ........................... 424/400; 424/40; 514/816
[58] Field of Search ................................ 424/400, 40, 43; 514/816

[56] References Cited

U.S. PATENT DOCUMENTS

| 4,855,511 | 8/1989 | Halpern et al. |
| 4,874,901 | 10/1989 | Halpern et al. |
| 5,114,714 | 5/1992 | Young et al. |
| 5,114,715 | 5/1992 | Young et al. |

FOREIGN PATENT DOCUMENTS

94/23727  10/1994  WIPO.

OTHER PUBLICATIONS

Ornstein, E. et al. "Desflurane and Isoflurane Have Similar Effects on Cerebral Blood Flow in Patients with Intracranial Mass Lesions" Anesthesiology, vol. 79, No. 3, Sep. 1993.
Ornstein, E. et al. "Desflurane and isoflurane have similar effects . . . " Anesthesiology, vol. 79 No. 3, 1993, pp. 498–502.

Primary Examiner—Gollamudi S. Kishore
Assistant Examiner—Brian K. Seidleck
Attorney, Agent, or Firm—Nixon & Vanderhye

[57] ABSTRACT

A high pressure pre-mixed analgesic anaesthetic gas composition comprising a life supporting gas and a volatile analgesic anaesthetic mixture; characterised in that the mixture comprises a first and a second anaesthetic analgesic, said first analgesic having blood/gas solubility co-efficient $\lambda$ significantly in excess of the $\lambda$ of the second analgesic.

10 Claims, No Drawings

ANAESTHETIC MIXTURES CONTAINING ENFLURANE OR ISOFLURANE IN COMBINATION WITH SEVOFLURANE OR DESFLURANE

This is 371 of International Patent Application PCT/GB95/02021, filed Aug. 25, 1995, and claiming priority based on British Patent Application No. 9418532.9, filed Sep. 14, 1994.

The present invention relates to anaesthetic gas mixtures and particularly to anaesthetic analgesic gas mixtures.

Entonox is a 50% admixture of oxygen and nitrous oxide and is used as a gaseous analgesic. Unfortunately nitrous oxide oxidizes the cobalt in Vitamin $B_{12}$ so rendering it inactive. Prolonged administration of nitrous oxide either continuously or intermittently, can cause megaloblastic anaemia, degeneration of the spinal cord and depression of white cell formation. The dosage required to produce this effect with regard to intermittent exposures is not known. A large number of patients who require daily wound dressings, or who are subjected to other brief painful procedures, receive Entonox. This is not a problem for a limited number of uses, but for repeated use the problems for accumulated toxicity become real and there is a need for a gaseous analgesic gas of a similar potency and speed of onset to Entonox, but without the potential cumulative toxicity of nitrous oxide.

In our British Patent Application No. 9418532.9, we have described the addition of isoflurane and other ether based anaesthetic gases to Entonox to allow for more prolonged pain relief. We have now found that under suitable conditions, nitrous oxide may be replaced completely by an admixture of at least two anaesthetic analgesic gases having the correct relative properties.

The speed and onset of a gaseous agent is related to its solubility in the blood. For an agent of low solubility, a small mass of gas is removed from the lung-gas space by the blood. A high partial pressure is therefore maintained in the lung space (Alveoli) which ensures in turn a high partial pressure of the agent in the blood.

The pharmacological effect of such an agent is determined by arterial blood partial pressure. Nitrous oxide has a rapid onset to action since it has a blood/gas solubility co-efficient $\lambda$ of 0.4. Halothane has as much slower onset of action ($\lambda=2.4$). Enflurane ($\lambda=1.9$) and Isoflurane ($\lambda=1.4$) are intermediate in onset while Sevoflurane ($\lambda=0.6$–0.7) and Desflurane ($\lambda=0.42$) have blood/gas solubility co-efficient close to that of nitrous oxide (0.46) and hence similar speeds of onset. The speed of onset is therefore predicated on an analgesic anaesthetic gas mixture incorporating agents with a fast onset and with a slower onset.

The time taken for the analgesic properties of a gaseous agent to wear off is determined again by blood/gas solubility but fast palinalgesia (offset of action) is not a desirable property for an analgesic since it is better if painful sensation returns gradually so that the patient can deal with it either by further self-administration or by mental readjustment. The ideal gaseous analgesic composition would therefore benefit from having a more soluble agent which delays analgesia and allows some accumulation of effect between inhalations. Inter alia, isoflurane has this effect when combined with Entonox as set out in our above-identified British Patent Application.

According therefore to the present invention, there is provided a high pressure pre-mixed analgesic anaesthetic gas composition comprising a life supporting gas and a volatile analgesic anaesthetic mixture, characterised in that the mixture comprises a first and second anaesthetic analgesic, said first analgesic having a blood/gas solubility co-efficient $\lambda$ significantly in excess of the $\lambda$ of the second analgesic. In one embodiment of the invention, the second analgesic may have a $\lambda$ value between about 25 to 50% of the first analgesic. Alternatively the first analgesic may have a blood/gas solubility co-efficient $\lambda$ above 1.0 and a second analgesic anaesthetic having a blood/gas solubility co-efficient below $\lambda 1.0$.

In a preferred embodiment, the $\lambda$ of the first analgesic may have a value above 1.3 while $\lambda$ of the second analgesic may have a value below 0.7.

Preferably, the volatile analgesic anaesthetics forming the composition are selected from volatile ether analgesic anaesthetics. The first analgesic may be adapted to prolong palinalgesia may be selected for example, from Enflurane or Isoflurane, while the second analgesic adapted to bring about rapid onset of analgesia may be selected from Sevoflurane and Desflurane.

The compounds in accordance with the present invention may comprise in addition to the life-supporting gas, up to 25% of the anesthetizing concentration of the first and second analgesics. Thus, for example, the mixture may comprise up to 0.3% Isoflurane and tip to 1.5% Desflurane. It is also recently been shown that the solvent properties of nitrogen at high pressure are similar to those of oxygen. It follows that in addition to medical grade oxygen, medical grade air may be utilized as a carrier for the anaesthetic analgesic compositions in accordance with the present invention. Thus, the life supporting gas may comprise oxygen and air in approximately equal amounts. Specifically, cylinders containing the desired admixture of anaesthetic analgesic compositions may be partially charged with 100% oxygen at, for example, 137 bar to 50% capacity, whereupon compressed air at medical grade is then added to a further 50%.

The invention will now be described by way of illustration only with reference to the following examples.

EXAMPLE 1

Preparation of gas mixtures

The applicants first made a mixture of approximately 0.3% Isoflurane (about 25% of anaesthetizing concentration). 1.5% Desflurane (about 25% of anaesthetizing concentration) with a balance of oxygen in a high pressure cylinder of 82.6 atmospheres absolute. These concentrations were chosen to give a dose equivalent in potency to that of Entonox.

The saturated vapour pressure of Desflurane is 93.3 kPa and that of isoflurane is 31.73 kPa. It follows that the vapour pressure in the cylinder of Desflurane exceeds its saturated vapour pressure to a significant degree and hence on cooling the cylinder, liquid precipitation occurs at about 4° C. This is not acceptable in a high pressure pre-mixed gaseous anaesthetic analgesic and hence a further cylinder at the same pressure (147 atomspheres) was mixed with 0.3% Isoflurane and 1% Desflurane. The partial pressures here are well below saturation and this mixture is stable to −3° C. It is believed however that higher pressures and gas air admixtures may allow higher percentages of the anaesthetic analgesic gas to be incorporated in higher pressure pre-mixed cylinders.

A gaseous analgesic capable of "relative" analgesia for use, for example, by dentists may also be formed with 0.2% Isoflurane and 0.7% Desflurane in oxygen or an oxygen/air mixture. This mixture is stable down to about −2° C.

EXAMPLE 2

Administration

The latter composition comprising oxygen, 0.3% Isoflurance and 1% Desflurane was administered to a patient on a surgical ward who could no longer tolerate Entonox. The patient presented with a substantial (about five inches deep) perianal abscess cavity due to Crohn's Disease of the bowel. Infection, while being under control required daily dressing changes which were very painful. The patient had been receiving Entonio for dressing changes but this was perceived as becoming more unacceptable as time went past.

Accordingly, with the patient's consent, the novel gas mixture was administered during change of dressings. The gas was self-administered by the patient who breathed it at about seventeen breaths per minute for five minutes during which time the dressing was changed. The patient expressed the view that the gas smelt different from Entonox having a distinctive taste and smell which were however not unpleasant. Pain relief from this mixture was about the same as that achieved with Entonox, whilst the patient expressed the wish that its use should be continued.

EXAMPLE 3

Administration

The following cases were assessed using a linear analogue score of memory for events, pain overall, the worst pain experienced and how much help the gas had been. Each patient was asked if he would use the gas again if the procedure was repeated. The nurse doing the dressing also scored the amount of help she got in performing the task. Each patient had received some opiate prior to the procedure.

Case 1—A 25 year old man with 20% burns to face, neck and back requiring wound dressings and removal of wound clips.

This man had his wound dressed on admission with only morphine analgesia (50 mg over a one hour period) and found it unbearable. In addition, the nurses doing the dressing found the experience very distressing. He received the gas three times for wound dressings. His memory for the dressing was hazy on each occasion and although the pain at times was close to intolerable (when the wound was showered with water) overall great relief was obtained. He gained considerable help from the gas. The dressing nurses also got considerable help from the gas with one describing it as "wonderful".

Case 2—A 64 year old lady with a leg ulcer revealing underlying tendons requiring wound dressing prior to skin grafting.

This woman had received wound dressings in the past and had found them very painful. She found that her memory of the dressing under inhalationial analgesia was clear. She got considerable pain relief and felt "calmed" by the gas. She would use the gas again. The nurse also found the gas to help her task.

Case 3—A 40 year old man who had a missile pass through his forearm causing considerable disruption. It had been reconstructed and skin grafted but there was considerable loss of joint function requiring twice daily physiotherapy to mobilise the joints.

This man has a clear memory for the procedures and remained co-operative with the physiotherapist. Initially he found the pain of the procedure severe, even with the gas. He got increasing amounts of help from pain, however, as the procedure was repeated. He wished to have the gas again on each occasion and in fact used it 6 times in three days and continues to do so. The physiotherapist has found the gas very helpful in that the patient no longer lifts himself off the bed in agony.

The use of mixtures of gaseous anaesthetics as analgesics has not been described in the prior art and neither has the administration of such mixtures from a single high pressure gas cylinder. It seems likely that at higher cylinder pressures, the saturated vapour pressure for the volatile agents can be exceeded while maintaining acceptable low temperature stability. With regard to this, we have noted that the potency to saturated vapour pressure ratio seems to be predictive as to suitability to agents for use in high pressure mixtures.

The invention relates therefore to a high pressure, pre-mixed analgesic anaesthetic gas, a method of its administration and to a high pressure pre-mixed analgesic anaesthetic gas mixture disposed in oxygen and optionally air, in a cylinder at high pressure.

We claim:

1. A high pressure pre-mixed analgesic anaesthetic gas composition comprising a life supporting gas and a volatile analgesic anaesthetic mixture comprising a first and a second anaesthetic analgesic, said first analgesic being present in an amount effective to prolong palinalgesia and said second analgesic being present in an amount effective to bring about the onset of analgesia.

2. A composition according to claim 1, wherein the first anaesthetic analgesic has a blood/gas solubility co-efficient $\lambda$ above 1.0 and a second analgesic anaesthetic has a blood/gas solubility co-efficient $\lambda$ below 1.0.

3. A composition according to claim 2, wherein $\lambda$ of the first analgesic has a value above 1.3 and wherein $\lambda$ of the second analgesic has a value below 0.7.

4. A composition according to claim 1 wherein the first and second analgesic are both selected from the group consisting of ether based volatile analgesic anaesthetics.

5. A composition according to claim 1 wherein the first analgesic is Enflurane or Isoflurane and the second analgesic is Sevoflurane or Desflurane.

6. A composition according to claim 1 comprising up to about 25% of the anaesthetizing amount of the first and second analgesics.

7. A composition according to claim 1 wherein the mixture comprises up to 0.3% Isoflurane and up to 1.5% Desflurane.

8. A composition according to claim 1 wherein the life supporting gas comprises oxygen and air in approximately equal amounts.

9. A composition according to claim 8, wherein the mixture is admixed with oxygen to 50% volume and subsequently about 50% by volume of air is added thereto.

10. The high pressure cylinder comprising a higher pressure premixed analgesic anaesthetic gas composition according to claim 1.

* * * * *